United States Patent [19]

Shoesmith, deceased

[11] Patent Number: Plant 5,969

[45] Date of Patent: May 5, 1987

[54] CHRYSANTHEMUM PLANT NAMED FIRELIGHT

[75] Inventor: Leonard H. Shoesmith, deceased, late of Westfield, England, by May V. Shoesmith, executrix

[73] Assignee: Ball Pan Am Plant Company, Parrish, Fla.

[21] Appl. No.: 746,800

[22] Filed: Jun. 20, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Firelight having flat capitulum form and anemone capitulum type; rich bronze flower color; diameter of 4 cm to 7 cm across face of flower; and, uniform eight week flowering response.

1 Drawing Figure

The present invention comprises a new and distinct cultivar of *Chrysanthemum morifolium* Ramat., hereinafter referred to by the cultivar name Firelight.

Firelight is a product of a planned breeding program which had the objective of creating new Chrysanthemum cultivars with a rich bronze color, anemone flower type, ability to produce good quality plants with center bud removed (CBR) in 6" pots in 8 weeks from short days, year around. Such traits in combination were not present or needed improvement in previously available commercial cultivars.

Firelight was originated from a hybridization made in a controlled breeding program by Leonard H. Shoesmith in Westfield, Woking, Great Britain in 1979. The male and female parents are unknown at this time.

Firelight was discovered and selected as one flowering plant within the progeny of the stated parentage by or under the supervision of Leonard H. Shoesmith in November of 1979 in a controlled environment in West Chicago, Ill.

The first act of asexual reproduction of Firelight was accomplished when vegetative cuttings were taken from the initial selection in February of 1980 in a controlled environment in West Chicago, Ill. by a technician working under formulations established and supervised by Leonard H. Shoesmith. Horticultural examination of selected units initiated February of 1980 has demonstrated that the combination of characteristics as herein disclosed for Firelight are firmly fixed and are retained through successive generations of asexual reproduction.

Firelight has not been observed under all possible environmental conditions. The phenotype may vary significantly with variations in environment such as temperature, light intensity and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Firelight which in combination distinguish this Chrysanthemum as a new and distinct cultivar:

(1) Flat capitulum form.

(2) Anemone flower type.

(3) Rich bronze color fading to a pleasant light bronze as plant ages; green eye.

(4) Diameter across face of flower is 4 cm to 7 cm.

(5) Uniform 8 week flowering response when grown as a center bud removed pot plant through October in the north and year around on the west coast and in the south.

(6) Height is 12" to 18" above edge of a 6" pot; height depends on the number of long days prior to bud initiation, maturity of the cutting and the temperature.

Of the many commercial cultivars known to the present inventor, the most similar in comparison to Firelight is Cirbronze, disclosed in U.S. Plant Pat. No. 4,292. In comparison to Cirbronze, Firelight is one week earlier, has a more orange bronze color, and has an anemone disc under most conditions. The habit and flat capitulum form are similar to those same characteristics of Cirbronze.

The accompanying photographic drawing shows typical inflorescence and foliage characteristics of Firelight. The photograph is in black and white except for a cluster of flowers which represent the true flower color of Firelight.

In the following description, color references are made to The Royal Horticultural Society Colour Chart. The color values were determined at approximately 12:00 noon on May 2, 1985 under inflorescent light at Bradenton, Fla.

Classification:

*Botanical.*—*Chrysanthemum morifolium,* Ramat., cv Firelight.

*Commercial.*—Center bud removed 6" pot mum.

I. INFLORESCENCE

A. Capitulum:

*Form.*—Flat.

*Type.*—Anemone.

*Diameter across face.*—4 cm to 7 cm.

B. Corolla of ray florets:

*Color (general tonality from a distance of three meters).*—Orange bronze.

*Color (upper surface).*—171A fresh; fades to 168C.

*Color (under surface).*—164B.

C. Corolla of disc florets:

*Color (mature).*—Golden bronze.

*Color (immature).*—Lime green.

D. Reproductive organs:

*Androecium.*—Present in disc florets only; insignificant.

*Gynoecium.*—One per both ray and disc floret.

II. PLANT

A. General appearance:

*Height.*—12″ to 18″ above the edge of a 6″ pot.

B. Foliage:

*Color* (*upper surface*).—147A.

*Color* (*under surface*).—147B.

*Shape.*—Deeply lobed, margin repand.

It is claimed:

1. A new and distinct cultivar of Chrysanthemum plant named Firelight, as described and illustrated, and particularly characterized by its flat capitulum form and anemone capitulum type; rich bronze flower color; diameter of 4 cm to 7 cm across face of flower; and, uniform eight week flowering response.

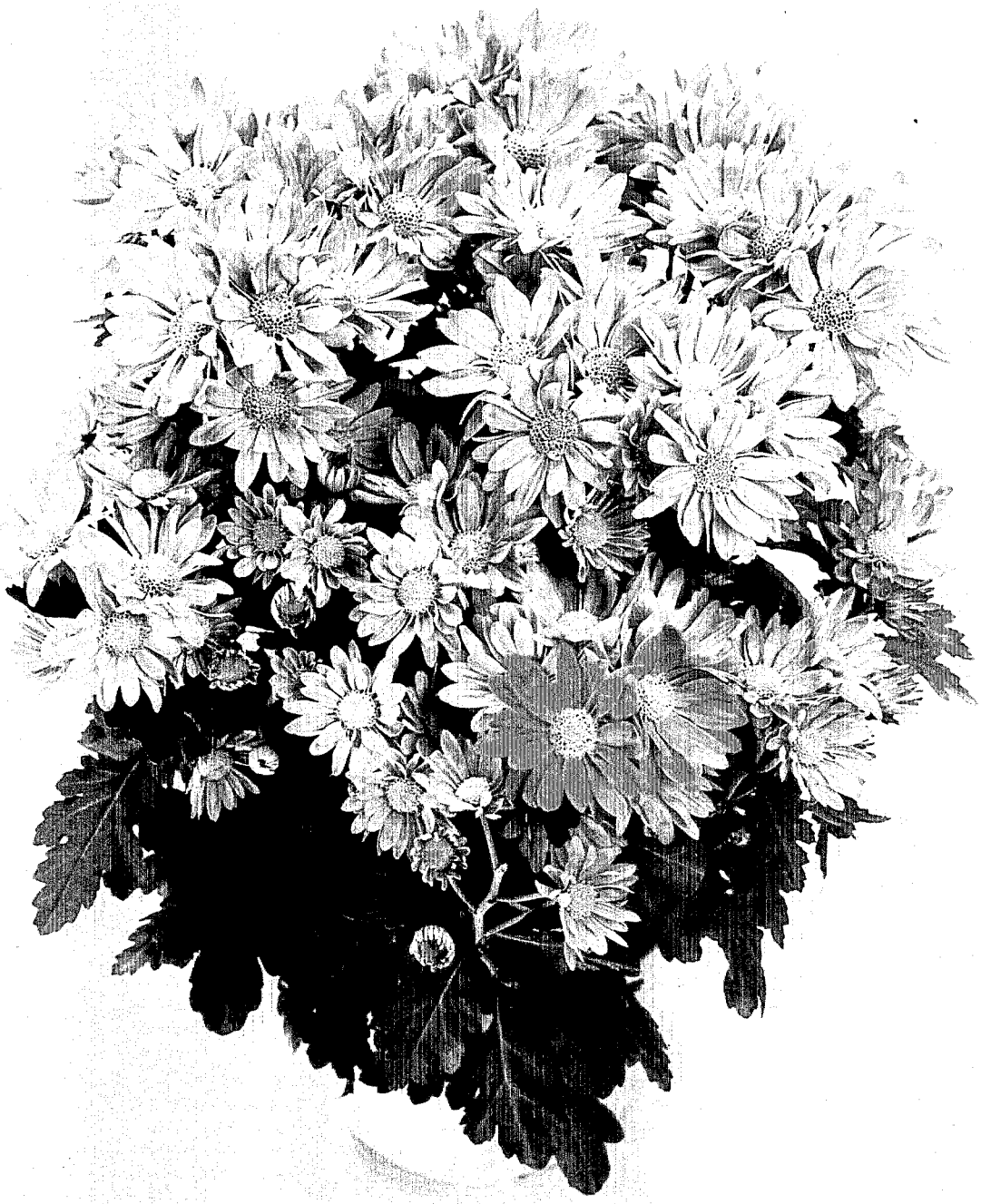

* * * * *